United States Patent
Arai et al.

(10) Patent No.: US 6,290,677 B1
(45) Date of Patent: Sep. 18, 2001

(54) MEDICINAL LIQUID INJECTION PORT

(75) Inventors: Yasuaki Arai, Nagoya; Yukihiko Sakaguchi; Yasunobu Izumi, both of Akita, all of (JP)

(73) Assignee: Sumitomo Bakelite Company Limited, Tokyo (JP)

( * ) Notice: Subject to any disclaimer, the term of this patent is extended or adjusted under 35 U.S.C. 154(b) by 0 days.

(21) Appl. No.: 09/101,987

(22) PCT Filed: Jan. 23, 1997

(86) PCT No.: PCT/JP97/00147

§ 371 Date: Jul. 22, 1998

§ 102(e) Date: Jul. 22, 1998

(30) Foreign Application Priority Data

Jan. 24, 1996 (JP) .................................................. 8-010478
Feb. 28, 1996 (JP) .................................................. 8-040890

(51) Int. Cl.$^7$ ................................................. A61M 5/178
(52) U.S. Cl. ...................................... 604/183; 604/93.01
(58) Field of Search ................................ 604/175, 181, 604/183, 533, 86, 905, 93.01

(56) References Cited

U.S. PATENT DOCUMENTS

| | | | |
|---|---|---|---|
| 4,929,236 | 5/1990 | Sampson | 604/175 |
| 5,092,849 | 3/1992 | Sampson | 604/175 |
| 5,176,641 | 1/1993 | Idriss | 604/133 |
| 5,632,729 | * 5/1997 | Cai et al. | 604/175 |
| 5,743,873 | * 4/1998 | Cai et al. | 604/175 |
| 5,755,780 | * 5/1998 | Finch, Jr. et al. | 604/175 |

FOREIGN PATENT DOCUMENTS

93/14797   8/1993   (WO) .
93/21988  11/1993   (WO) .

* cited by examiner

*Primary Examiner*—Anhtuan T. Nguyen
*Assistant Examiner*—Jeremy Thissell
(74) *Attorney, Agent, or Firm*—Smith, Gambrell & Russell, LLP

(57) ABSTRACT

A medicinal liquid injection port having an internal space for storing a medicinal liquid, a medicinal liquid inlet which communicates with the internal space, a septum which seals the medicinal liquid inlet, a medicinal liquid outflow path which communicates with the internal space, a connector being provided at the end of the medicinal liquid outflow path, and a protective lock, used in connecting a catheter, combined therewith, wherein the main body of the port has a concave part only in the direction of the medicinal liquid outflow path, the connector is placed in the concave part, and an external appearance is a form of an approximately integral body with the outer periphery of the port main body when the protective lock is fitted to the concave part of the port main body, or the medicinal liquid injection port which, when viewed from side, shows a form bulging upward and downward.

11 Claims, 4 Drawing Sheets

MEDICINAL LIQUID INJECTION PORT

TECHNICAL FIELD

The present invention relates to a subcutaneously imbeddable medicinal liquid injection system used for injecting a medicinal liquid into a specific site in the body of a patient continuously for a long period at given time intervals in, for example, the intra-arterial injection of anti-cancer drugs in the chemotherapy of progressive cancer patients, intravenous injection for nutrients feeding, administration of analgesics to the pulpa dura mater or the like for relief of pain, and administration of insulin to diabetic patients.

BACKGROUND ART

To cope with malignant tumors which cannot be excised, chemotherapy by anti-cancer drug administration has been practiced. However, since systemic administration of the drug causes serious side reactions, methods of selective administration have been used in which either the tip of a catheter is kept staying at the upper stream of the artery which leads to the site of the tumor while the end of the catheter is kept exposed outside the body as the inlet of the anti-cancer drug, or the catheter is re-inserted at each time of anti-cancer drug administration (intra-arterial therapy). In sustained injection of a high calorie infusion solution previously used, also, the tip of the catheter was kept staying in the central vein and the end of the catheter was exposed outside the body as the inlet of the fluid therapy injection (IVH).

Consequently, the prevention of infection through the wound of the skin at which the catheter has been inserted has been a long-standing problem. On the other hand, it is very difficult to keep the wounded part of the skin always clean in practical life; moreover, the presence of the catheter and the wound imposes restriction to the free movement, bathing, etc. of the patient. Thus, these situations have been a serious obstacle to the returning of the patient to the public community.

To solve the above-mentioned problems, a catheter assembly of subcutaneous imbedding type which can be used while being kept staying in the body for a long period has been developed. This catheter assembly comprises a port main body having an internal space for storing a medicinal liquid, a medicinal liquid inlet provided with an elastic body which communicates with the internal space, and a medicinal liquid outflow path provided with a connector, and a catheter having a lumen for medicinal liquid injection formed therein, the catheter being joined to the connector such that the lumen communicates with the liquid outflow path, and a protective lock for fixing the catheter and preventing it from kinking (folding) being joined by fitting thereto so as to cover the catheter joining part of the port main body.

The catheter assembly of subcutaneous imbedding type is kept in the body at a state wherein the catheter is inserted into the intended blood vessel and the medicinal liquid injection port is fixed in the subcutaneous tissue. In injecting a medicinal liquid, the medicinal liquid inlet of the liquid injection port is confirmed by palpation on the skin surface and the elastic body of the liquid inlet is needled with an injection needle thereby to feed the medicinal liquid into the port main body and inject the liquid into the intended blood vessel or the like via the catheter.

In the catheter assembly of the prior art, however, the connector is attached to the outer periphery of the port main body and resultantly the protective lock, which is connected and fixed by means of screw fitting, etc., protrudes further than the end of the connector to prevent the kink of the catheter which might be caused by the tip of the connector. Accordingly, when the catheter assembly of subcutaneous imbedding type is imbedded subcutaneously, an imbedding space which can accommodate only the periphery of the port main body is insufficient for the purpose and a deep incision must be made which corresponds to the space including the protective lock on the vertical line of the catheter. This not only imposes a heavy burden on the patient but makes it difficult for the operator to confirm the medicinal liquid inlet. Moreover, the longer the line including the port main body and the protective lock (that is, the longer the hard parts), the more difficult for the assembly to follow the movement of the patient, resulting in increased risk of occurrence of various troubles, such as the kink of the catheter.

The sites in which the medicinal liquid injection port is to be imbedded are mainly the chest, abdomen and thigh. In recent years, both the intra-arterial therapy and the IVH are mainly conducted by making use of the subclavian artery or vein and hence the port is mainly imbedded in the chest region.

When the medicinal liquid injection port of the prior art is viewed from side, the upper face is convex and the bottom face is flat. FIG. 5 is a sectional view of the prior medicinal liquid injection port imbedded subcutaneously, which shows a considerable protrusion of the skin. This causes much invasion when the injection port is imbedded in a site with thin subcutaneous fat, such as the chest region. Particularly when it is imbedded to a slender patient, the top of the skin is rubbed by clothes, which often causes rubefaction and inflammation.

DISCLOSURE OF THE INVENTION

The object of the present invention is to solve the problems as mentioned above, that is, to provide a medicinal liquid injection port which can be imbedded in a space afforded by incising merely the part corresponding to the outer periphery of the port main body because the outer periphery of the port including the protective lock approximately conforms to the outer periphery of the port main body and which can be easily imbedded by the operator, is less invasive to the patient, tends to cause less various troubles, such as the kink of the catheter and hence is safer, and further to provide a medicinal liquid injection port which is in the form of a convex lens bulging upward and downward when viewed from side and hence the body tissues located above and below the port bulge uniformly, and which consequently can be imbedded subcutaneously without imposing excessive tension on the upper side skin alone and is less invasive to the patient.

Thus, the present invention provides a medicinal liquid injection port comprising an internal space for storing a medicinal liquid, a medicinal liquid inlet which communicates with the internal space, a septum which seals the medicinal liquid inlet, a medicinal liquid outflow path which communicates with the internal space, a connector being provided at the end of the medicinal liquid outflow path, and a protective lock, used in connecting a catheter, combined therewith, wherein the main body of the port has a concave part only in the direction of the medicinal liquid outflow path, the connector is placed in the concave part, and an external appearance is a form of an approximately integral body with the outer periphery of the port main body when the protective lock is fitted to the concave part of the port main body, and wherein the fitted faces of the port and the protective lock are a concave face and a convex face, respectively, which fit to each other without a gap.

The present invention further provides a medicinal liquid injection port comprising an internal space for storing a medicinal liquid, a medicinal liquid inlet which communicates with the internal space, a septum which seals the medicinal liquid inlet, a medicinal liquid outflow path which communicates with the internal space, a connector being provided at the end of the medicinal liquid outflow path, and a protective lock, used in connecting a catheter, combined therewith, wherein the form of the port viewed from side bulges upward and downward and wherein, when viewed from side, the part of the maximum outer diameter is positioned within the range of 30% above and 30% below the center relative to the thickness.

BEST MODE FOR CARRYING OUT THE INVENTION

The present invention is described in detail below with reference to accompanying Drawings, but the invention is not limited thereto.

Figure 1:
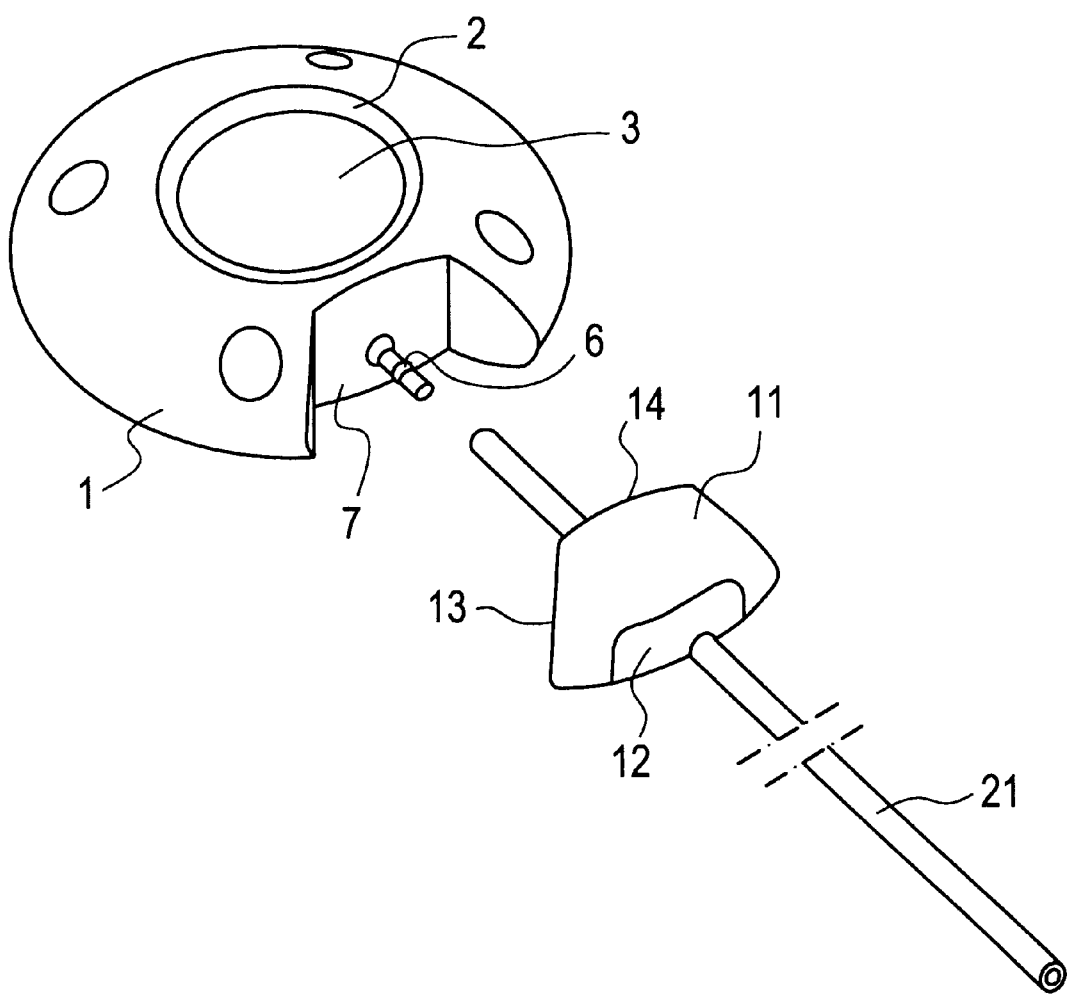
FIG. 1 is a perspective view showing a medicinal liquid injection port of one example of the present invention.
Figure 2A:
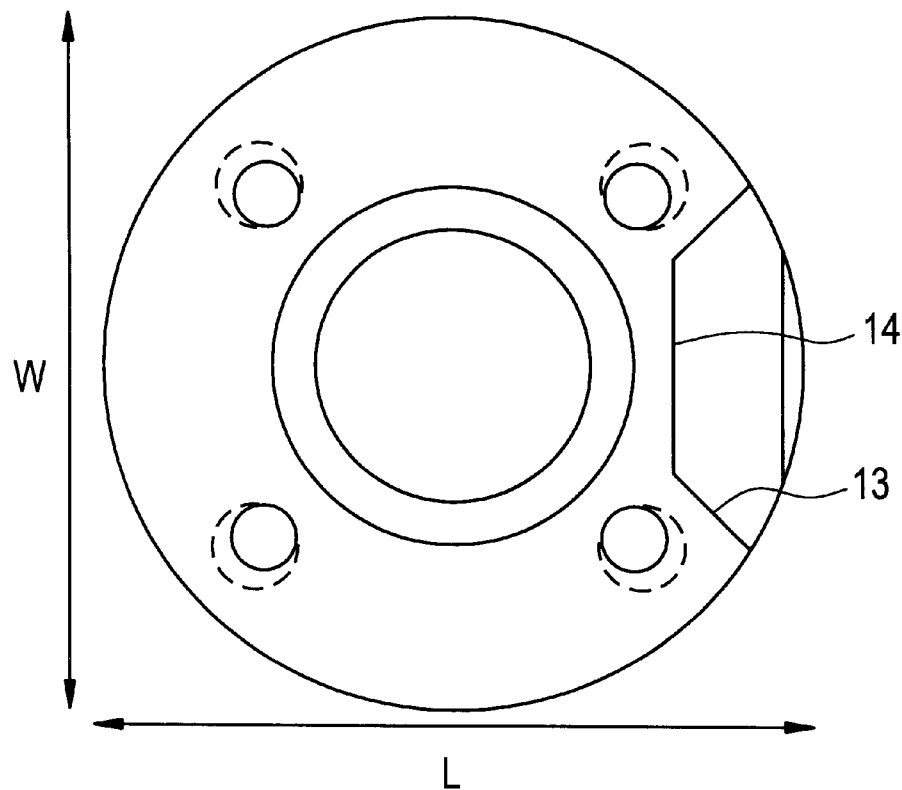
FIG. 2 shows a medicinal liquid injection port of one example of the present invention, (a) being a top view and (b) being a sectional view.
Figure 2B:
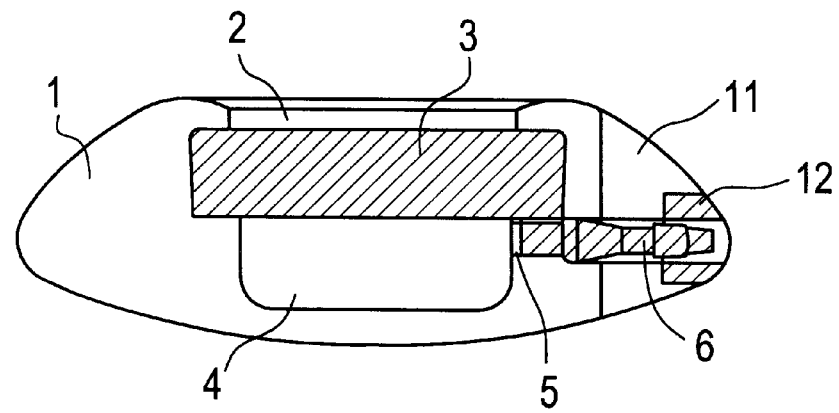

As shown in FIGS. 1 and 2, the medicinal liquid injection port of the present invention comprises a port main body 1 and a protective lock 11. The port main body 1 has an internal space 4 for storing a medicinal liquid, a medicinal liquid inlet 2, above the space 4, provided with a septum 3 which seals the medicinal liquid inlet, and a medicinal liquid outflow path 5 in one radial direction. The port main body 1 has a concave part 7, relative to the outer periphery, in the above-mentioned direction, and a connector 6 is provided to the center of the concave part 7. Thus, the external appearance of the port main body 1 is a form of disk from which a part thereof has been eliminated. The medicinal liquid outflow path 5, which discharges the medicinal liquid therethrough according to necessity, may be provided, in one preferred embodiment, with a one-way valve to prevent back flow.

The port main body 1, when viewed from side, has a form which bulges both upward and downward, and the maximum outer diameter part of the body is preferably positioned within the range of 30% above and 30% below the center relative to the thickness. Though invasion to patients is minimum when the maximum outer diameter part conforms to the center, then sometimes the bulging of the skin is too low, which makes it difficult to find the position of the imbedded medicinal liquid injection port. Therefore, the maximum outer diameter part is desirably positioned within the range of 5–15% below the center.

The material of the port main body 1 needs to be excellent in biocompatibility and may be, for example, resins such as polyurethane resin, polyether sulfone resin and silicone rubber, metals such as stainless steel and titanium, and combinations thereof. The material for the septum 3, which seals the medicinal liquid inlet, is preferably an elastomer, more preferably an elastic substance having a self-sealability and may be, for example, rubbers, such as silicone rubber, isoprene rubber and latex rubber; but soft poly(vinyl chloride) resins and polyurethane resins can also be used so long as they are excellent in puncture resistance and biocompatibility. The material for the connector 6 is preferably a metal, such as stainless steel and titanium, because of its excellent strength, but the material is not limited thereto. The port main body 1 is assembled from the above-mentioned constituent members by means of insert molding, adhesion, melt-bonding, etc.

Next, the protective lock 11 is explained below. The external appearance of the protective lock corresponds to the eliminated part of the above-mentioned disk form of the port main body 1. The material for the protective lock may be similar to that for the port main body 1 mentioned above, but the fitting part 13 which fits to the port main body 1 and the pressure-fixing part 14 which pressure-fixes a catheter 21, which are positioned at the rear end, are preferably made of a hard material, and a part at the front end which contacts with the catheter is preferably provided with a catheter contacting part (elastic part) 12 in order to be able to follow the movement of the catheter and prevent kinking and other troubles.

Accordingly, when the port main body 1 and the protective lock 11 are fitted to each other, the external appearance of the combined two members assumes the form of a disk showing no protrusion of the protective lock 11. The fitting parts of the port main body 1 and the protective lock 11 are preferably respectively formed such that they can be fitted by means of undercut, etc. to attain more stable fitting, but they are not particularly restricted thereto.

Figure 3A:
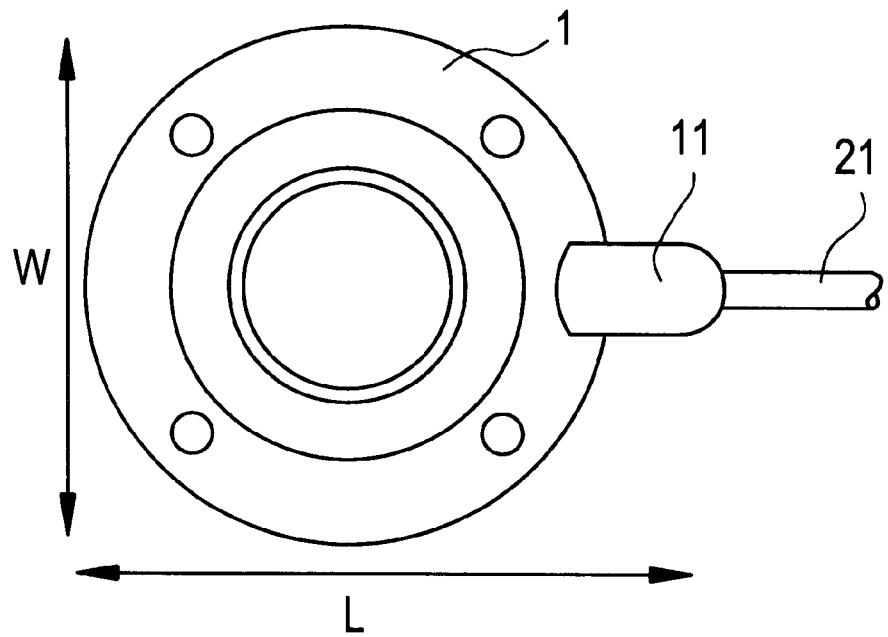
FIG. 3 shows a medicinal liquid injection port of the prior art, (a) being a top view and (b) being a sectional view.
Figure 3B:
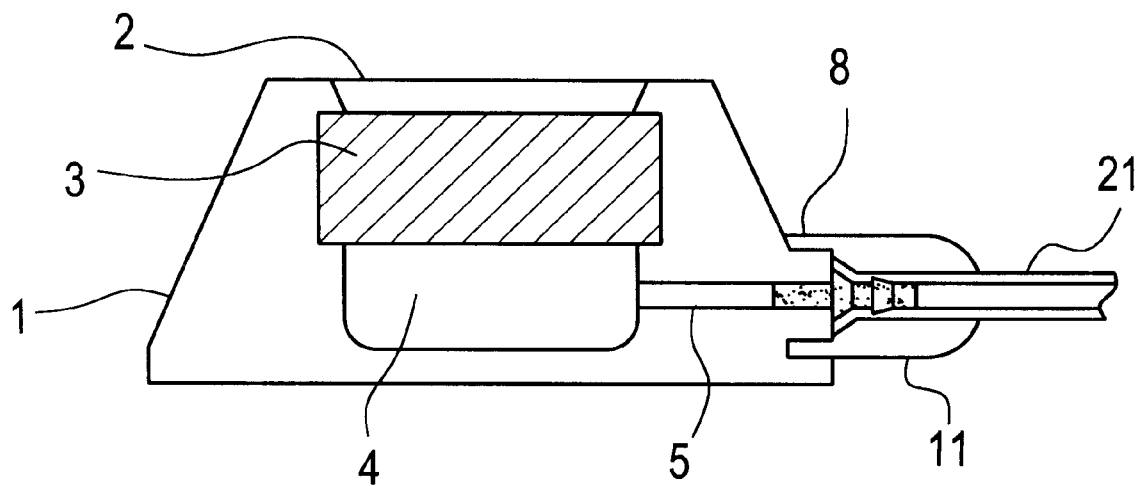

The method of assembling the medicinal liquid injection port according to the present invention is described below with reference to FIG. 1. A catheter 21 which has been passed through the protective lock 11 beforehand is inserted into and connected to the connector 6 of the port main body 1, and then the protective lock 11 is slided and fixed to the port main body 1 by fitting. In the medicinal liquid injection port of the present Example assembled as described above, when viewed from above, the length L is approximately equal to the width W, whereas in the medicinal liquid injection port of the prior art, as shown in FIG. 3, the length L is greater than the width W.

Figure 4:
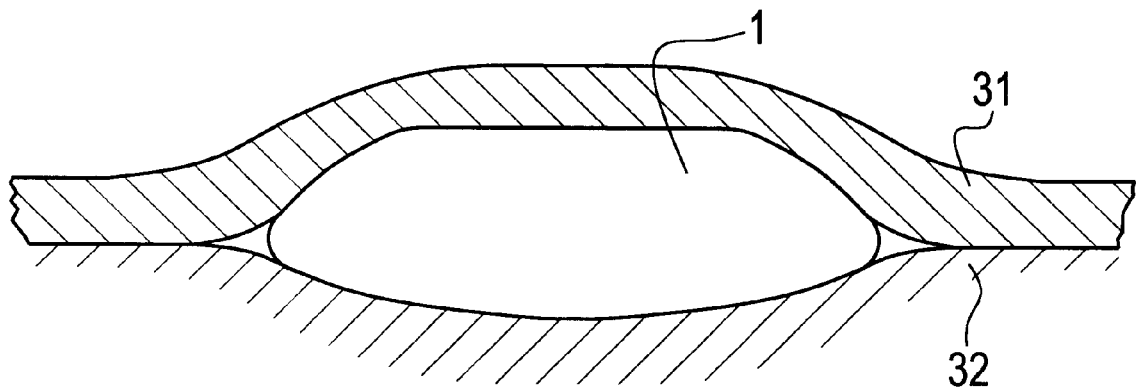
FIG. 4 is a sectional side view showing the state of subcutaneous imbedding of a medicinal liquid injection port of one example of the present invention.
Figure 5:
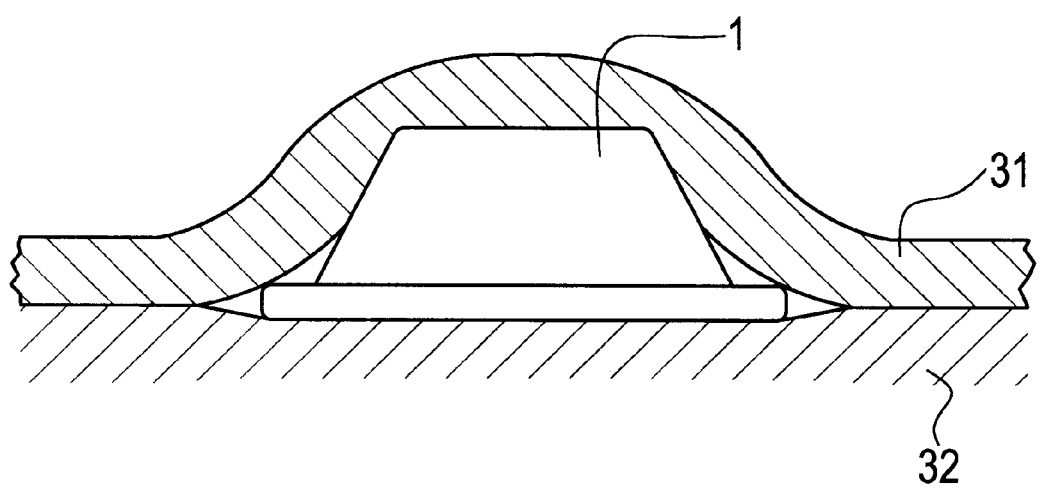
FIG. 5 is a sectional side view showing the state of subcutaneous imbedding of a medicinal liquid injection port of the prior art.

When viewed from side, as shown in FIG. 4, the medicinal liquid injection port is imbedded between the subcutaneous fat layer 31 and the fascia layer 32. The medicinal liquid inlet 2 of the liquid injection port is confirmed by palpation on the skin surface and the septum 3 sealing the medicinal liquid inlet 2 i needled with an injection needle thereby to feed a medicinal liquid into the port main body, and the medicinal liquid is injected into the intended blood vessel or the like via the catheter 21.

INDUSTRIAL APPLICABILITY

As set forth above, the medicinal liquid injection port according to the present invention requires a smaller (shallower) incision space for imbedding and hence can be imbedded by the operator with ease and is less invasive to the patient. Moreover, it hardly causes various troubles including catheter kinking. Thus, the medicinal liquid injection port is very useful as an instrument which can make the selective medicinal liquid injection to be conducted more safely.

Furthermore, the medicinal liquid injection port according to the present invention can be imbedded subcutaneously without applying excessive tension to the skin of the patient and is very useful as an instrument which can make the selective medicinal liquid injection performed with less invasion and more safety.

What is claimed is:

1. A medicinal liquid injection port comprising a main body with a curved outer periphery, an internal space for storing a medicinal liquid, a medicinal liquid inlet which communicates with the internal space, a septum which seals the medicinal liquid inlet, a medicinal liquid outflow path which communicates with the internal space, a connector being provided at the end of the medicinal liquid outflow path, and a protective lock, used in connecting a catheter, combined therewith, wherein the main body of the port has a concave part in the direction of the medicinal liquid outflow path relative to an outer periphery of the main body of the port and the protective lock is placed in said concave part, wherein the fitted faces of the main body of the port and the protective lock are a concave face and a convex face, respectively, and fit to each other without a gap and the outward facing portion of the protective lock completes the curve of the outer periphery of the main body of the medicinal port without protruding the protective lock when said protective lock is fitted to the concave part of the main body of the port.

2. The medicinal liquid injection port according to claim 1, wherein the protective lock is provided on a front end side with a catheter contacting part and the catheter contacting part is an elastic body.

3. The medicinal liquid injection port according to claim 1, which, when viewed from side, shows a form bulging upward and downward.

4. A medicinal liquid injection port comprising an internal space for storing a medicinal liquid, a medicinal liquid inlet which communicates with the internal space, a septum which seals the medicinal liquid inlet, a medicinal liquid outflow path which communicates with the internal space, a connector being provided at the end of the medicinal liquid outflow path, and a protective lock, used in connecting a catheter, combined therewith, wherein the medicinal liquid injection port shows, when viewed from a side, a form bulging upward and downward wherein, when viewed from a side, the maximum outer diameter part of the downward bulging form is positioned within a range below the center relative to the thickness that is greater than zero.

5. The medicinal liquid injection port according to claim 4, wherein the form is the form of a convex lens.

6. The medicinal liquid injection port according to claim 4 wherein, when viewed from a side, the maximum outer diameter part is positioned within the range of 30% above and 30% below the center relative to the thickness.

7. The medicinal liquid injection port according to claim 4 wherein, when viewed from a side, the maximum outer diameter part is positioned within the range of up to 30% below the center relative to the thickness.

8. The medicinal liquid injection port according to claim 4 wherein, when viewed from a side, the maximum outer diameter part is positioned within the range of up to 15% below the center relative to the thickness.

9. The medicinal liquid injection port according to claim 4 wherein, when viewed from a side, the maximum outer diameter part is positioned within the range of 5–30% below the center relative to the thickness.

10. The medicinal liquid injection port according to claim 4 wherein, when viewed from a side, the maximum outer diameter part is positioned within the range of 5–15% below the center relative to the thickness.

11. A medicinal liquid injection port comprising a main body with a curved outer periphery, an internal space for storing a medicinal liquid, a medicinal liquid inlet which communicates with the internal space, a septum which seals the medicinal liquid inlet, a medicinal liquid outflow path which communicates with the internal space, a connector being provided at the end of the medicinal liquid outflow path, and a protective lock, used in connecting a catheter, combined therewith, wherein the medicinal liquid injection port shows, when viewed from a side, a form bulging upward and downward wherein the form is the form of a convex lens and when viewed from a side, the maximum outer diameter part is positioned within the range of 5–15% below the center relative to the thickness.

* * * * *